United States Patent
Hsiao et al.

(10) Patent No.: US 7,811,752 B2
(45) Date of Patent: Oct. 12, 2010

(54) PLASMA OR SERUM MARKER AND PROCESS FOR DETECTION OF CANCER

(75) Inventors: Wen-Luan Wendy Hsiao, Hong Kong (CN); Sze-Chuen Cesar Wong, Hong Kong (CN)

(73) Assignee: The Hong Kong University of Science and Technology, Kowloon, Hong Kong (CN)

( * ) Notice: Subject to any disclaimer, the term of this patent is extended or adjusted under 35 U.S.C. 154(b) by 194 days.

(21) Appl. No.: 10/516,864

(22) PCT Filed: Jun. 27, 2003
(Under 37 CFR 1.47)

(86) PCT No.: PCT/US03/20587

§ 371 (c)(1),
(2), (4) Date: Mar. 30, 2006

(87) PCT Pub. No.: WO2004/002294

PCT Pub. Date: Jan. 8, 2004

(65) Prior Publication Data

US 2007/0092874 A1    Apr. 26, 2007

Related U.S. Application Data

(60) Provisional application No. 60/392,191, filed on Jun. 28, 2002.

(51) Int. Cl.
*C07H 21/04* (2006.01)
*C12Q 1/68* (2006.01)

(52) U.S. Cl. .................... 435/6; 435/91.1; 435/91.2; 536/23.1; 536/24.3

(58) Field of Classification Search .............. None
See application file for complete search history.

(56) References Cited

U.S. PATENT DOCUMENTS

2002/0106685 A1    8/2002    Henning et al.

OTHER PUBLICATIONS

Wong et al. Clinical Cancer Research, vol. 10, pp. 1613-1617, Mar. 2004.*
Osman et al (Clin Cancer, Res. vol. 12, No. 11, pp. 3374-3380, Jun. 2006).*
Fleischhacker et al. (Biocheimica et Biophysica Acta, vol. 1775, pp. 181-232, 2007).*
Mulcahy et al. Cancer and mutant DNA in blood plasma. The Lancet. Sep. 7, 1996, vol. 348, pp. 28.
Anker et al. Detection of circulating tumour DNA in the blood(plasma/serum) of cancer patients. Cancer and Metastasis Reviews. 1999, vol. 18, pp. 65-73.
Valizadeh et al. Expression of E-cadherin-associate molecules (alpha, beta and gamma-catenins a p 120) in colorectal polyps. Am. J. Pathology. Jun. 1997, vol. 150, No. 6 pp. 1977-1984.
Qin et al. The prognostic molecular markers in hepatocellular carcinoma. World AJ. Gastroenterol. 2002, vol. 8, No. 3, pp. 385-392.

* cited by examiner

*Primary Examiner*—Jeanine A Goldberg
(74) *Attorney, Agent, or Firm*—George G. Wang; Wilkinson & Grist

(57) ABSTRACT

This disclosures provides, in one aspect, a method for detecting non-clinically diagnosed cancer in a patient. In one embodiment, the method includes extracting blood serum or plasma from the patient, and then detecting beta-catenin RNA in the blood serum or plasma. In addition, in this embodiment, the method includes determining the presence of the cancer based on the detected beta-catenin RNA. In another aspect, this disclosure provides another embodiment of a method for detecting non-clinically diagnosed cancer in a patient. In this embodiment, the method includes extracting blood serum or plasma from the patient, and then detecting beta-catenin DNA in the blood serum or plasma. In addition, in this embodiment, the method includes determining the presence of the cancer based on the detected beta-catenin DNA. Related methods for detecting non-clinically diagnosed cancer in a patient comprising detecting beta-catenin-associated gene RNA, and beta-catenin-associated gene DNA, in the blood serum or plasma are also disclosed.

11 Claims, 3 Drawing Sheets

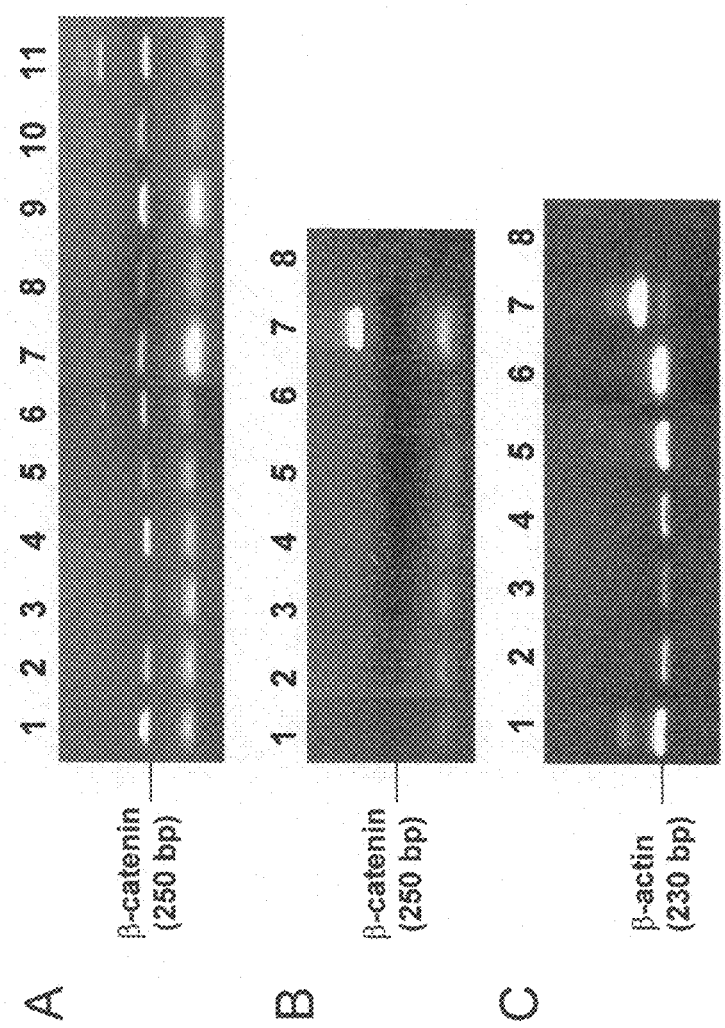
Figure 2A-C

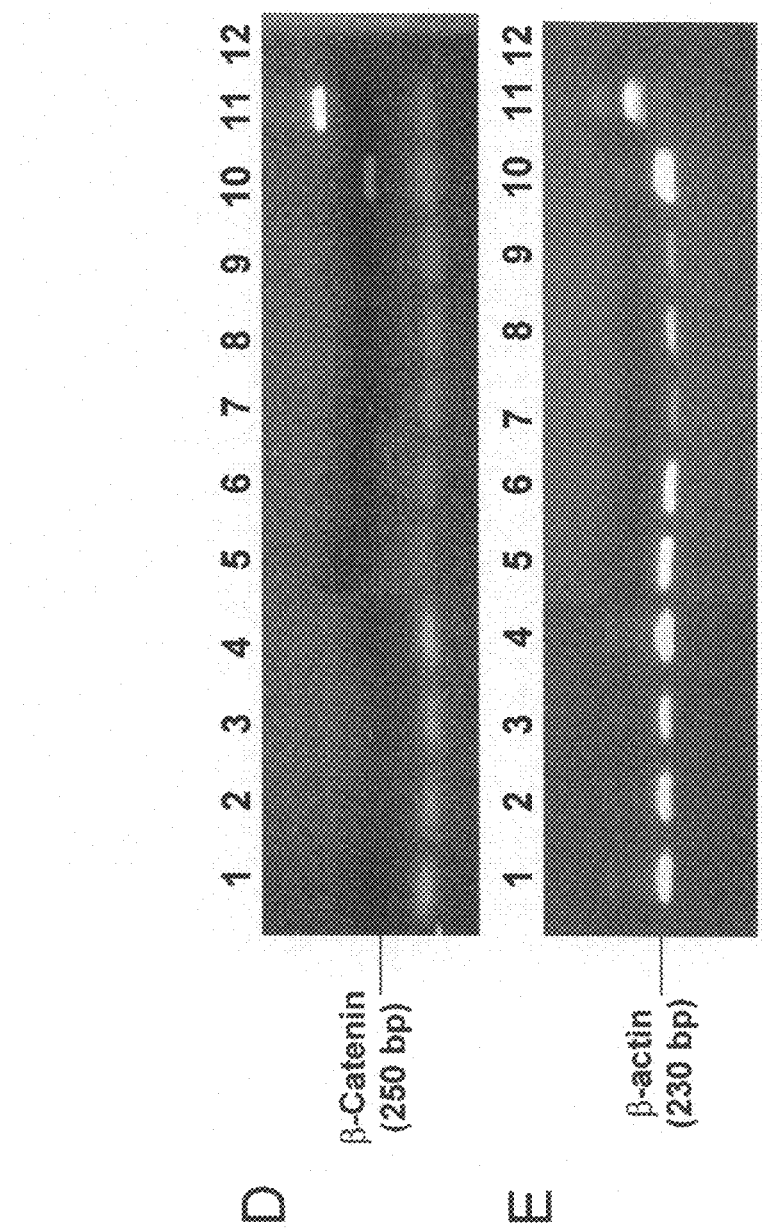

SEQUENCE LISTING

<160> NUMBER OF SEQ ID NOS: 13

<210> SEQ ID NO 1
<211> LENGTH: 3697
<212> TYPE: DNA
<213> ORGANISM: Homo sapiens

<400> SEQUENCE: 1

| | | | | | |
|---|---|---|---|---|---|
| cccacgcgtc | cgggcagcag | cgttggcccg | gccccgggag | cggagagcga | ggggaggcgg | 60 |
| agacggagga | aggtctgagg | agcagcttca | gtccccgccg | agccgccacc | gcaggtcgag | 120 |
| gacggtcgga | ctcccgcggc | gggaggagcc | tgttcccctg | agggtatttg | aagtatacca | 180 |
| tacaactgtt | ttgaaaatcc | agcgtggaca | atggctactc | aagctgattt | gatggagttg | 240 |
| gacatggcca | tggaaccaga | cagaaaagcg | gctgttagtc | actggcagca | acagtcttac | 300 |
| ctggactctg | gaatccattc | tggtgccact | accacagctc | cttctctgag | tggtaaaggc | 360 |
| aatcctgagg | aagaggatgt | ggatacctcc | caagtcctgt | atgagtggga | cagggatttt | 420 |
| tctcagtcct | tcactcaaga | acaagtagct | gatattgatg | acagtatgc | aatgactcga | 480 |
| gctcagaggg | tacgagctgc | tatgttccct | gagacattag | atgagggcat | gcagatccca | 540 |
| tctacacagt | ttgatgctgc | tcatcccact | aatgtccagc | gtttggctga | accatcacag | 600 |
| atgctgaaac | atgcagttgt | aaacttgatt | aactatcaag | atgatgcaga | acttgccaca | 660 |
| cgtgcaatcc | ctgaactgac | aaaactgcta | aatgacgagg | accaggtggt | ggttaataag | 720 |
| gctgcagtta | tggtccatca | gctttctaaa | aaggaagctt | ccagacacgc | tatcatgcgt | 780 |
| tctcctcaga | tggtgtctgc | tattgtacgt | accatgcaga | atacaaatga | tgtagaaaca | 840 |
| gctcgttgta | ccgctgggac | cttgcataac | ctttcccatc | atcgtgaggg | cttactggcc | 900 |
| atctttaagt | ctggaggcat | tcctgccctg | gtgaaaatgc | ttggttcacc | agtggattct | 960 |
| gtgttgtttt | atgccattac | aactctccac | aacctttttat | tacatcaaga | aggagctaaa | 1020 |
| atggcagtgc | gtttagctgg | tgggctgcag | aaaatggttg | ccttgctcaa | caaaacaaat | 1080 |
| gttaaattct | tggctattac | gacagactgc | cttcaaattt | tagcttatgg | caaccaagaa | 1140 |
| agcaagctca | tcatactggc | tagtggtgga | ccccaagctt | tagtaaatat | aatgaggacc | 1200 |
| tatacttacg | aaaaactact | gtggaccaca | agcagagtgc | tgaaggtgct | atctgtctgc | 1260 |
| tctagtaata | agccggctat | tgtagaagct | ggtggaatgc | aagctttagg | acttcacctg | 1320 |
| acagatccaa | gtcaacgtct | tgttcagaac | tgtctttgga | ctctcaggaa | tctttcagat | 1380 |
| gctgcaacta | acaggaagg | gatgaaggt | ctccttggga | ctcttgttca | gcttctgggt | 1440 |
| tcagatgata | taaatgtggt | cacctgtgca | gctggaattc | tttctaacct | cacttgcaat | 1500 |
| aattataaga | acaagatgat | ggtctgccaa | gtgggtggta | tagaggctct | tgtgcgtact | 1560 |
| gtccttcggg | ctggtgacag | ggaagacatc | actgagcctg | ccatctgtgc | tcttcgtcat | 1620 |
| ctgaccagcc | gacaccaaga | agcagagatg | gcccagaatg | cagttcgcct | tcactatgga | 1680 |
| ctaccagttg | tggttaagct | cttacaccca | ccatcccact | ggcctctgat | aaaggctact | 1740 |
| gttggattga | ttcgaaatct | tgcccttttgt | cccgcaaatc | atgcacctt | gcgtgagcag | 1800 |
| ggtgccattc | cacgactagt | tcagttgctt | gttcgtgcac | atcaggatac | ccagcgccgt | 1860 |
| acgtccatgg | gtgggacaca | gcagcaattt | gtggagggg | tccgcatgga | agaaatagtt | 1920 |
| gaaggttgta | ccggagccct | tcacatccta | gctcgggatg | ttcacaaccg | aattgttatc | 1980 |
| agaggactaa | ataccattcc | attgtttgtg | cagctgcttt | attctcccat | tgaaaacatc | 2040 |

```
caaagagtag ctgcaggggt cctctgtgaa cttgctcagg acaaggaagc tgcagaagct    2100
attgaagctg agggagccac agctcctctg acagagttac ttcactctag gaatgaaggt    2160
gtggcgacat atgcagctgc tgttttgttc cgaatgtctg aggacaagcc acaagattac    2220
aagaaacggc tttcagttga gctgaccagc tctctcttca gaacagagcc aatggcttgg    2280
aatgagactg ctgatcttgg acttgatatt ggtgcccagg gagaacccct tggatatcgc    2340
caggatgatc ctagctatcg ttcttttcac tctggtggat atggccagga tgccttgggt    2400
atggacccca tgatggaaca tgagatgggt ggccaccacc tggtgctga ctatccagtt     2460 gatgggctgc cagatctggg gcatgcccag gacctcatgg atgggctgcc tccaggtgac    2520
agcaatcagc tggcctggtt tgatactgac ctgtaaatca tcctttaggt aagaagtttt    2580
aaaaagccag tttgggtaaa atactttttac tctgcctaca gaacttcaga aagacttggt   2640
tggtagggtg ggagtggttt aggctatttg taaatctgcc acaaaaacag gtatatactt    2700
tgaaaggaga tgtcttggaa cattggaatg ttctcagatt tctggttgtt atgtgatcat    2760
gtgtggaagt tattaacttt aatgtttttt gccacagctt ttgcaactta atactcaaat    2820
gagtaacatt tgctgtttta aacattaata gcagcctttc tctctttata cagctgtatt    2880
gtctgaactt gcattgtgat tggcctgtag agttgctgag agggctcgag gggtgggctg    2940
gtatctcaga aagtgcctga cacactaacc aagctgagtt tcctatggga acaattgaag    3000
taaacttttt gttctggtcc ttttggtcg aggagtaaca atacaaatgg attttgggag     3060
tgactcaaga agtgaagaat gcacaagaat ggatcacaag atggaattta gcaaacccta    3120
gccttgcttg ttaaaatttt tttttttttt tttaagaat atctgtaatg gtactgactt     3180
tgcttgcttt gaagtagctc ttttttttttt tttttttttt tttttttgc agtaactgtt    3240 ttttaagtct ctcgtagtgt taagttatag tgaatactgc tacagcaatt tctaattttt    3300
aagaattgag taatggtgta gaacactaat taattcataa tcactctaat taattgtaat    3360
ctgaataaag tgtaacaatt gtgtagcctt tttgtataaa atagacaaat agaaaatggt    3420
ccaattagtt tcctttttaa tatgcttaaa ataagcaggt ggatctattt catgttttg     3480 atcaaaaact atttgggata tgtatgggta gggtaaatca gtaagaggtg ttatttggaa    3540
ccttgttttg gacagtttac cagttgcctt ttatcccaaa gttgttgtaa cctgctgtga    3600
tacgatgctt caagagaaaa tgcggttata aaaaatggtt cagaattaaa cttttaattc    3660
attcaaaaaa aaaaaaaaaa aaaaaaaaaa aaaaaaa                             3697
```

<210> SEQ ID NO 2
<211> LENGTH: 3778
<212> TYPE: DNA
<213> ORGANISM: Homo sapiens

<400> SEQUENCE: 2

```
ccatttcctc ctcctagccg gactggaggg agacaaagca gcgcccgtct gcttcgggcc     60
tctggaattt agcgctcgcc cagctagccg cagaaatgac tgctgtccat gcaggcaaca    120
taaacttcaa gtgggatcct aaaagtctag agatcaggac tctggcagtt gagagactgt    180
tggagcctct tgttcacag gttacaaccc ttgtaaacac caatagtaaa gggccctcta     240
ataagaagag aggtcgttct aagaaggccc atgttttggc tgcatctgtt gaacaagcaa    300
ctgagaattt cttggagaag ggggataaaa ttgcgaagga gagccagttt ctcaaggagg    360
agcttgtggc tgctgtagaa gatgttcgaa aacaaggtga tttgatgaag gctgctgcag    420
```

-continued

```
gagagttcgc agatgatccc tgctcttctg tgaagcgagg caacatggtt cgggcagctc    480
gagctttgct ctctgctgtt acccggttgc tgattttggc tgacatggca gatgtctaca    540
aattacttgt tcagctgaaa gttgtggaag atggtatctt gaagttgagg aatgctggca    600
atgaacaaga cttaggaatc cagtataaag ccctaaaacc tgaagtggat aagctgaaca    660
ttatggcagc caaaagacaa caggaattga agatgttggc catcgtgat cagatggctg    720 cagctagagg aatcctgcag aagaacgttc cgatcctcta tactgcatcc caggcatgcc    780
tacagcaccc tgatgtcgca gcctataagg ccaacaggga cctgatatac aagcagctgc    840
agcaggcggt cacaggcatt tccaatgcag cccaggccac tgcctcagac gatgcctcac    900
agcaccaggg tggaggagga ggagaactgg catatgcact caataacttt gacaaacaaa    960
tcattgtgga ccccttgagc ttcagcgagg agcgctttag gccttccctg gaggagcgtc   1020
tggaaagcat cattagtggg gctgccttga tggccgactc gtcctgcacg cgtgatgacc   1080
gtcgtgagcg aattgtggca gagtgtaatg ctgtccgcca ggccctgcag gacctgcttt   1140
cggagtacat gggcaatgct ggacgtaaag aaagaagtga tgcactcaat tctgcaatag   1200
ataaaatgac caagaagacc agggacttgc gtagacagc ccgcaaagct gtcatggacc   1260
acgtttcaga ttcttttcctg gaaaccaatg ttccactttt ggtattgatt gaagctgcaa   1320
agaatggaaa tgagaaagaa gttaaggagt atgcccaagt tttccgtgaa catgccaaca   1380
aattgattga ggttgccaac ttggcctgtt ccatctcaaa taatgaagaa ggtgtaaagc   1440
ttgttcgaat gtctgcaagc cagttagaag ccctctgtcc tcaggttatt aatgctgcac   1500
tggctttagc agcaaaacca cagagtaaac tggcccaaga gaacatggat cttttttaaag   1560 aacaatggga aaaacaagtc cgtgttctca cagatgctgt cgatgacatt acttccattg   1620
atgacttctt ggctgtctca gagaatcaca ttttggaaga tgtgaacaaa tgtgtcattg   1680
ctctccaaga gaaggatgtg gatggcctgg accgcacagc tggtgcaatt cgaggccggg   1740
cagcccgggt cattcacgta gtcacctcag agatggacaa ctatgagcca ggagtctaca   1800
cagagaaggt tctggaagcc actaagctgc tctccaacac agtcatgcca cgttttactg   1860
agcaagtaga agcagccgtg gaagccctca gctcggaccc tgcccagccc atggatgaga   1920
atgagtttat cgatgcttcc cgcctggtat atgatggcat ccgggacatc aggaaagcag   1980
tgctgatgat aaggacccct gaggagttgg atgactctga ctttgagaca gaagattttg   2040
atgtcagaag caggacgagc gtccagacag aagacgatca gctgatagct ggccagagtg   2100
cccgggcgat catggctcag cttccccagg agcaaaaagc gaagattgcg gaacaggtgg   2160
ccagcttcca ggaagaaaag agcaagctgg atgctgaagt gtccaaatgg gacgacagtg   2220
gcaatgacat cattgtgctg gccaagcaga tgtgcatgat tatgatggag atgacagact   2280
ttacccgagg taaaggacca ctcaaaaata tcggatgt catcagtgct gccaagaaaa   2340
ttgctgaggc aggatccagg atggacaagc ttggccgcac cattgcagac cattgccccg   2400
actcggcttg caagcaggac ctgctggcct acctgcaacg catcgccctc tactgccacc   2460
agctgaacat ctgcagcaag gtcaaggccg aggtgcagaa tctcggcggg agcttgttg   2520 tctctggggt ggacagcgcc atgtccctga tccaggcagc caagaacttg atgaatgctg   2580
tggtgcagac agtgaaggca tcctacgtcg cctctaccaa ataccaaaag tcacagggta   2640
tggcttccct caaccttcct gctgtgtcat ggaagatgaa ggcaccagag aaaaagccat   2700
tggtgaagag agagaaacag gatgagacac agaccaagat taaacgggca tctcagaaga   2760
agcacgtgaa cccggtgcag gccctcagcg agttcaaagc tatggacagc atctaagtct   2820
```

```
gcccaggccg ccgcccccca cccctcgggg ctcctgaata tcagtcactg ttcgtcactc    2880
aaatgaattt gctaaataca acactgatac tagattccac agggaaatgg gcagactgaa    2940
ccagtccagg tggtgaattt tccaagaaca tagtttaagt tgattaaaaa tgcttttaga    3000
atgcaggagc ctacttctag ctgtattttt tgtatgctta aataaaaata aaaattcata    3060
accaaagaga atcccacatt agcttgttag taatgctctg accaagccga gatgcccatt    3120
ctcttagtga tggcggcgtt agggtttgag agaagggaat ttggctcaac ttcagttgag    3180
agggtgcagt ccagacagct tgactgcttt taaatgacca agatgaccct gtggtaagca    3240
acctgggcat cttaggaagc agtccctgga gaaggcatgt tcccagaaag gtctctggag    3300
ggacaaactc actcagtaaa acataatgta tcatgaagaa aactgattct ctatgacatg    3360
aaatgaaaat tttaatgcat tgttataatt actaatgtac gctgctgcag acattaata    3420 aagttgcttt tttaggctac agtgtctcga tgccataatc agaacacact ttttttcctc    3480
tttctcccag cttcaaatgc aaattcatca ttgggctcac ttctaataac tgcagtgttt    3540
cccgccttgg gcttgcagca gaaaaacctg acaacatagt gtttgctaag gcagtaattt    3600
agactttacc ttatttgtga ttactgtagt gattgattga ttgattacta ttaactacaa    3660
ggtataattt actatcacct tatttaaatt ttatgaatta atttgaatgt ttttacact    3720 aactaacttt tcccaataaa gtccactatg aaaccacgac aaaaaaaaaa aaaaaaaa     3778

<210> SEQ ID NO 3
<211> LENGTH: 4828
<212> TYPE: DNA
<213> ORGANISM: Homo sapiens

<400> SEQUENCE: 3
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga atttttgaaga   300 ttgcaccggt cgacaaagga cagcctattt ttccctcgac cccgattcaa agtgggcac     360 agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgcccatca ggcctccgtt tctggaatcc aagcagaatt      540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaaagaag gcaaggtttt ctacagcatc actggccaag agctgacac      720 acccccctgtt ggtgtcttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga atgacaacaa     900
gcccgaattc acccaggagg tctttaaggg gtctgtcatg gaaggtgctc ttccaggaac     960
ctctgtgatg gaggtcacag ccacagacgc ggacgatgat gtgaacacct acaatgccgc    1020
catcgcttac accatcctca gccaagatcc tgagctccct gacaaaaata tgttcaccat    1080
taacaggaac acaggagtca tcagtgtggt caccactggg ctggaccgag agagtttccc    1140
```

```
tacgtatacc ctggtggttc aagctgctga ccttcaaggt gaggggttaa gcacaacagc    1200
aacagctgtg atcacagtca ctgacaccaa cgataatcct ccgatcttca atcccaccac    1260
gtacaagggt caggtgcctg agaacgaggc taacgtcgta atcaccacac tgaaagtgac    1320
tgatgctgat gcccccaata ccccagcgtg ggaggctgta tacaccatat tgaatgatga    1380
tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500 ggtaccttt gaggtctctc tcaccacctc cacagccacc gtcaccgtgg atgtgctgga    1560
tgtgaatgaa gcccccatct tgtgcctcc tgaaaagaga gtggaagtgt ccgaggactt    1620
tggcgtgggc caggaaatca catcctacac tgcccaggag ccagacacat ttatggaaca    1680
gaaaataaca tatcggattt ggagagacac tgccaactgg ctggagatta atccggacac    1740
tggtgccatt ccactcgggg ctgagctgga cagggaggat tttgagcacg tgaagaacag    1800
cacgtacaca gccctaatca tagctacaga caatggttct ccagttgcta ctggaacagg    1860
gacacttctg ctgatcctgt ctgatgtgaa tgacaacgcc cccataccag aacctcgaac    1920
tatattcttc tgtgagagga tccaaagcc tcaggtcata aacatcattg atgcagacct    1980
tcctcccaat acatctccct tcacagcaga actaacacac ggggcgagtg ccaactggac    2040
cattcagtac aacgacccaa cccaagaatc tatcattttg aagccaaaga tggcttaga    2100 ggtgggtgac tacaaaatca atctcaagct catggataac cagaataaag accaagtgac    2160 cacccttagag gtcagcgtgt gtgactgtga aggggccgcc ggcgtctgta ggaaggcaca    2220
gcctgtcgaa gcaggattgc aaattcctgc cattctgggg attcttggag gaattcttgc    2280
tttgctaatt ctgattctgc tgctcttgct gtttcttcgg aggagagcgg tggtcaaaga    2340
gcccttactg cccccagagg atgacacccg ggacaacgtt tattactatg atgaagaagg    2400
aggcggagaa gaggaccagg actttgactt gagccagctg cacagggcc tggacgctcg    2460 gcctgaagtg actcgtaacg acgttgcacc aaccctcatg agtgtccccc ggtatcttcc    2520
ccgccctgcc aatcccgatg aaattggaaa ttttattgat gaaatctga aagcggctga    2580 tactgacccc acagcccgc cttatgattc tctgctcgtg tttgactatg aaggaagcgg    2640
ttccgaagct gctagtctga gctccctgaa ctcctcagag tcagacaaag accaggacta    2700
tgactacttg aacgaatggg gcaatcgctt caagaagctg gctgacatgt acggaggcgg    2760
cgaggacgac tagggactc gagagaggcg ggccccagac ccatgtgctg ggaaatgcag    2820
aaatcacgtt gctggtggtt tttcagctcc cttcccttga gatgagtttc tggggaaaaa    2880
aaagagactg gttagtgatg cagttagtat agctttatac tctctccact ttatagctct    2940
aataagtttg tgttagaaaa gtttcgactt atttcttaaa gctttttttt ttttcccatc    3000
actctttaca tggtggtgat gtccaaaaga tacccaaatt ttaatattcc agaagaacaa    3060
ctttagcatc agaaggttca cccagcacct tgcagatttt cttaaggaat tttgtctcac    3120
ttttaaaaag aagggagaa gtcagctact ctagttctgt tgttttgtgt atataatttt    3180
ttaaaaaaaa tttgtgtgct tctgctcatt actacactgg tgtgtccctc tgcctttttt    3240 tttttttta agacagggtc tcattctatc ggccaggctg gagtgcagtg gtgcaatcac    3300
agctcactgc agccttgtcc tcccaggctc aagctatcct tgcacctcag cctcccaagt    3360
agctgggacc acaggcatgc accactacgc atgactaatt ttttaaatat tgagacggg    3420 gtctccctgt gttacccagg ctggtctcaa actcctgggc tcaagtgatc ctcccatctt    3480
ggcctcccag agtattggga ttacagacat gagccactgc acctgcccag ctccccaact    3540
```

-continued

| | |
|---|---|
| ccctgccatt tttaagaga cagtttcgct ccatcgccca ggcctgggat gcagtgatgt | 3600 |
| gatcatagct cactgtaacc tcaaactctg gggctcaagc agttctccca ccagcctcct | 3660 |
| ttttattttt ttgtacagat ggggtcttgc tatgttgccc aagctggtct taaactcctg | 3720 |
| gcctcaagca atccttctgc cttggccccc caaagtgctg ggattgtggg catgagctgc | 3780 |
| tgtgcccagc ctccatgttt taatatcaac tctcactcct gaattcagtt gctttgccca | 3840 |
| agataggagt tctctgatgc agaaattatt gggctctttt agggtaagaa gtttgtgtct | 3900 |
| ttgtctggcc acatcttgac taggtattgt ctactctgaa gacctttaat ggcttccctc | 3960 |
| tttcatctcc tgagtatgta acttgcaatg ggcagctatc cagtgacttg ttctgagtaa | 4020 |
| gtgtgttcat taatgtttat ttagctctga agcaagagtg atatactcca ggacttagaa | 4080 |
| tagtgcctaa agtgctgcag ccaaagacag agcggaacta tgaaagtggg gcttggagat | 4140 |
| ggcaggagag cttgtcattg agcctggcaa tttagcaaac tgatgctgag gatgattgag | 4200 |
| gtgggtctac ctcatctctg aaaattctgg aaggaatgga ggagtctcaa catgtgtttc | 4260 |
| tgacacaaga tccgtggttt gtactcaaag cccagaatcc ccaagtgcct gcttttgatg | 4320 |
| atgtctacag aaaatgctgg ctgagctgaa cacatttgcc caattccagg tgtgcacaga | 4380 |
| aaaccgagaa tattcaaaat tccaaatttt ttcttaggag caagaagaaa atgtggccct | 4440 |
| aaaggggtt agttgagggg taggggtag tgaggatctt gatttggatc tctttttatt | 4500 |
| taaatgtgaa tttcaacttt tgacaatcaa agaaaagact tttgttgaaa tagctttact | 4560 |
| gtttctcaag tgttttggag aaaaaaatca accctgcaat cacttttttgg aattgtcttg | 4620 |
| attttcggc agttcaagct atatcgaata tagttctgtg tagagaatgt cactgtagtt | 4680 |
| ttgagtgtat acatgtgtgg gtgctgataa ttgtgtattt tctttggggg tggaaaagga | 4740 |
| aaacaattca agctgagaaa agtattctca aagatgcatt tttataaatt ttattaaaca | 4800 |
| attttgttaa accataaaaa aaaaaaaa | 4828 |

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
atttgatgga gttggacatg g                                     21

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
agctacttgt tcttgagtga a                                     21

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6

```
tgatttgatg gagttggaca t                                              21
```

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7

```
cattgcatac tgtccatcaa t                                              21
```

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8

```
aaatcgtgcg tgacattaag g                                              21
```

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9

```
atgatggagt tgaaggtagt t                                              21
```

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10

```
tcaatgggtc atatcacaga t                                              21
```

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11

```
ctgcattctg actttcagta a                                              21
```

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12

```
cctctgcggt gccaagcctc                                                20
```

<210> SEQ ID NO 13
<211> LENGTH: 22
<212> TYPE: DNA
<213> ORGANISM: Artificial

```
-continued

<220> FEATURE:
<223> OTHER INFORMATION: Primer

<400> SEQUENCE: 13
tgtgggcaaa cttgtggtag ca                                              22
```

PLASMA OR SERUM MARKER AND PROCESS FOR DETECTION OF CANCER

CROSS-REFERENCE TO RELATED APPLICATION

This non-provisional International Patent Application claims priority from U.S. Provisional Application Ser. No. 60/392,191, filed on Jun. 28, 2002, and entitled "Plasma or Serum Marker and Process for Detection of Cancer", which is commonly owned with the present application and incorporated herein by reference for all purposes.

FIELD OF THE INVENTION

The present invention relates to a PCR based process in detection of blood plasma or serum marker for diagnosis, early detection, monitoring and population screening for cancer and, more particularly, detection of β-catenin RNA and DNA in blood plasma or serum for colorectal cancer.

BACKGROUND OF THE INVENTION

Colorectal cancer (CRC) is one of the most common malignancies worldwide. The number of new cases of CRC has been increasing rapidly since 1975. More than 70% of CRC cases develop from sporadic adenomas or adenomatous polyps. Early detection and surgical removal of polyps is believed to be the most effective way to prevent benign polyps from developing into malignant tumors and thereby reducing mortality caused by CRC.

Traditional screening methods for colorectal cancer include sigmoidoscopy, fecal occult blood testing, colonscopy and double contrast barium enema. However, these traditional methods suffer from limitations and are invasive, high cost, of low predictive value or result in low detection rates. For example, WO0142504, the teachings of which are incorporated herein by reference, discloses a multi-reaction process for detection of extracellular tumor associated nucleic acid in blood plasma or serum. Further advances are desirable.

β-catenin protein was initially identified through its interaction with cadherins. Recent evidence shows that it acts as a transcriptional factor and plays a key role in the Wnt-signaling pathway Willert & Nusse, 1998). It has been demonstrated that accumulation of cytoplasmic and nuclear β-catenin signaling is tightly associated with the genesis of a wide variety of tumors. (Morin, 1999).

It has been discovered that using immunohistochemical staining that levels of nuclear β-catenin are highly correlated with he purported sequential stages in colorectal carcinogenesis with positive staining observed in 0% of normal tissues, 8% of polyps, 92% of adenomas and 100% of carcinomas. It has been further discovered that the nuclear β-catenin signal appears to clearly differentiate the polyps (non-adenomatous polyps) from adenomas (adenomatous polyps). This would be a useful marker for clinical diagnosis, or early detection of CRC, with the adenoma being considered as endpoint for risk factor. However, this diagnostic method based on the evaluation of nuclear β-catenin requires colonscopic procedure, then surgical removal of the suspected tissues.

Accordingly, there is a need for an effective, less invasive, more accurate test for early detection of cancer. The present invention meets this need.

SUMMARY OF THE INVENTION

The present invention provides a PCR (Polymerase Chain Reaction) based method or process in the detection of serum or plasma marker RNA and DNA related to beta-catenin providing an effective, less evasive and more accurate test for the diagnosis, early detection, monitoring, and population screening of colorectal and other cancer types. It will be appreciated that this method of detection of beta-catenin RNA and DNA in blood serum can be applied to other plasma and serum RNA and DNA encoded for beta-catenin associated proteins. In one embodiment, the RNA or DNA is derived from genes encoded beta-catenin, alpha-catenin, E-cadherin and other beta-catenin associated proteins.

The process of the present invention comprises detecting blood serum or plasma RNA or/and DNA from a human or animal as a tool in the diagnosis, early detection, monitoring, treatment and population screening of neoplastic diseases at various progression and clinical stages. One advantage of the present invention is the non-invasive nature of the method, and a second advantage is improved accessibility of sample collections and sensitivity Details of multiple embodiments of the invention are set forth below. These embodiments are for illustrative purposes only and the principle of the invention can be implemented in other embodiments. Other features and advantages of this invention will become apparent from the following description and examples.

BRIEF DESCRIPTION OF THE DRAWINGS

For a more complete understanding, reference is now made to the following detailed description taken in conjunction with the accompanying drawings. It is emphasized that some components may not be illustrated for clarity of discussion. Reference is now made to the following descriptions taken in conjunction with the accompanying drawings, in which:

FIG. 2a and FIG. 2b illustrate detection of blood plasma β-catenin RNA from patients for colorectal adenoma using RT-PCR.

FIG. 2c illustrate detection of blood plasma β-actin RNA from patients for colorectal adenoma using RT-PCR. FIG.2d and FIG.2e illustrate detection of plasma β-catenin and β-actin RNA from healthy individuals using RT-PCR.

DETAILED DESCRIPTION OF THE INVENTION

Figure 1:
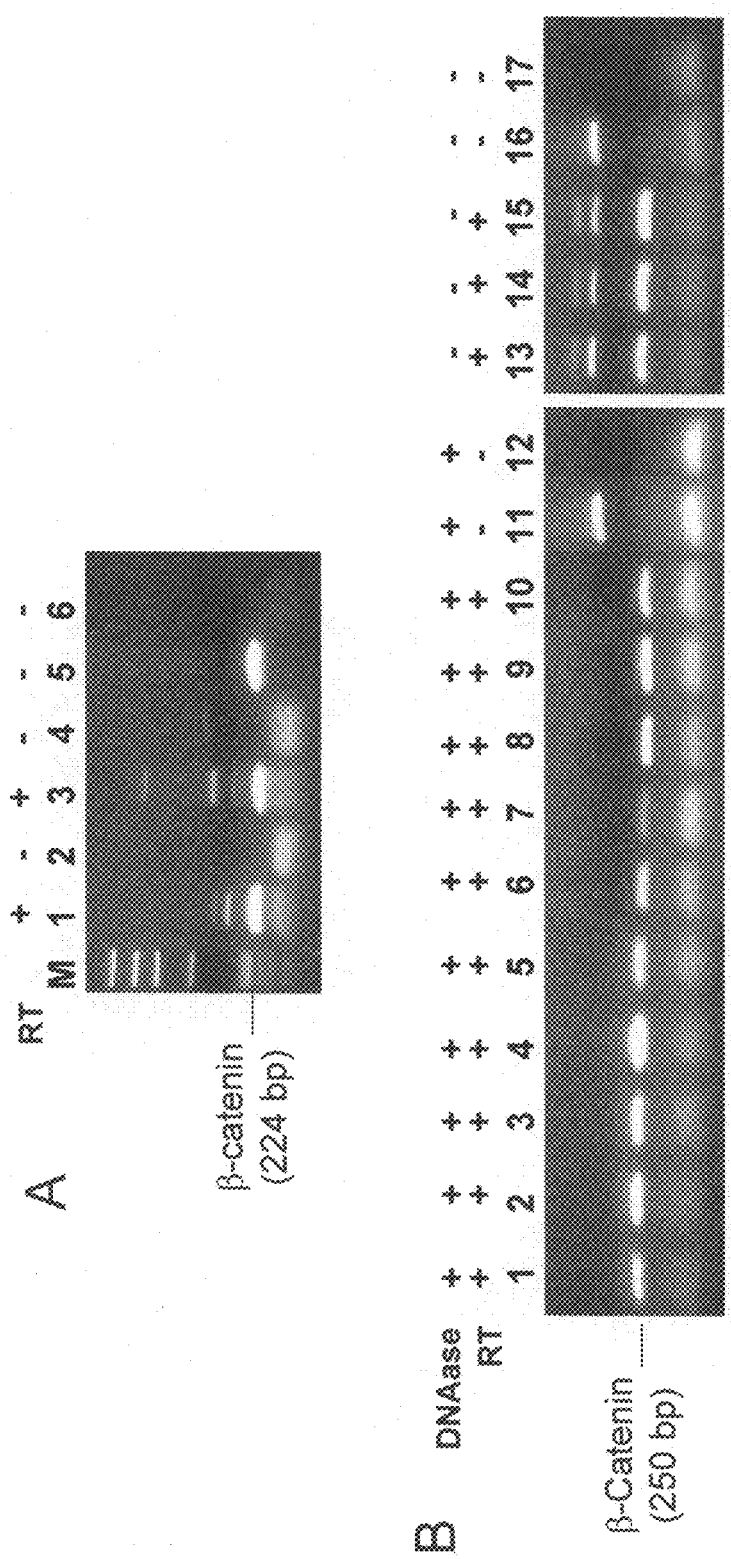
FIG. 1a, FIG. 1b and FIG. 1c illustrate detection of β-catenin RNA from plasma of colorectal carcinoma patients using RT-PCR.

The search for sensitive and specific biomarkers for early detection of colorectal cancer has been discovered in the present invention. The advanced understanding of the molecular mechanism underlying the carcinogenesis of colorectal cancer has helped to identify a few oncogenes and tumor suppressors as potential clinical biomarkers of colorectal cancer development and early detection. These include k-ras, APC, p53, MCC, DCC genes. However, none of the candidate markers alone can provide satisfactory detection rate. The recent PCR-based detections of K-ras, APC and p53 mutations of in the blood samples of cancer patients have indeed greatly increased the accessibility of sample collections. However, the rate of detection is generally lower than that observed with primary tumors. For instance, in a study of 14 patients with colorectal cancer, out of seven confirmed k-ras mutations, the same mutation was found in 6 patients' serum. The serum positive rate was 86% (Anker 1997). Another study showed that serum positive rate for loss of heterozygosity (LOH), microsatellite instability, k-ras and p53 mutations were 0, 0, 19, and 70% respectively (Hibi 1998). Similar results have been obtained with other types of cancers, in which the genetic alterations found in serum DNA (deoxyribonucleic acid) tend to be lower than those found in primary tumors (Kopreski 2001; Sozzi 1999; von Knobloch 2001).

Compared with other related studies, the use of serum β-catenin DNA in the present invention for early detection of colorectal cancer may fulfill the criteria of being a marker for early detection: 1. The marker is differentially present in blood of normal, and premalignant or tumor-bearing patients; 2. The method has the capacity to detect adenomatous polyps as small as 4 mm in diameter; 3. The method is simple with high degree of accuracy; 4. The amount of blood sample required is small (2-5 ml), and sample collection is through non-invasive, normal blood-drawing procedure. Thus, it has been suggested in the present invention that β-catenin DNA levels, along with β-catenin RNA levels, in blood serum or plasma could provide one answer to the quest for an effective, accurate test for colorectal cancer, using equipment and reagents already readily available—hence appropriate for widespread population screening, early detection, and disease monitoring of this increasingly common cancer.

EXAMPLES

The following examples are intended to illustrate, but not limit the embodiments of the invention described herein. Specifically, in the following discussion, numerous specific details are set forth to provide a thorough understanding of the present disclosure. However, those skilled in the art will appreciate that some of the techniques herein may be practiced without such specific details. In other instances, well-known elements or specific details have been condensed or omitted altogether inasmuch as detail discussions of these features are not considered necessary to obtain a complete understanding of the disclosure, and are considered to be within the understanding of persons of ordinary skill in the relevant field of art.

Example 1

β-Catenin RNA was Detected in all Plasma Samples of Patients with Colorectal Carcinoma To detect the presence of plasma β-catenin, RT-PCR (reverse transcription-polymerase chain reactions) were preformed on two blood samples from patients with carcinoma using Primer #1 that would yield a 224 bp of exon 3 region of the gene. An RNA sample extracted from carcinoma tumor expressing high level of β-catenin was included as positive control. Results showed that two plasma and the positive control RNA samples yielded a 224 bp band in the presence, but not in the absence of, reverse transcriptase (RT) in the reaction (FIG. 1a). RT-PCR analysis was preformed on the other 10 plasma RNA samples using the intron spanning primers (Primer #2, Table 2).

Data showed that a 250 bp fragment was clearly detected in all 10 patient plasma samples (FIG. 1a, lanes 1-10), suggesting the presence of β-catenin RNA in the circulating blood of carcinoma patients. The data also showed that the reaction is RT-dependent (FIG. 1b, lane 12). A genomic DNA sample was included as a positive control for PCR reaction and a 450 bp band appeared as expected (FIG. 1b, lane 11).

To prove that the 250 bp band was derived from the RNA, instead of DNA templates in the plasma, tests were performed on the three remaining plasma RNA samples without prior treatment with DNase I.

Two PCR products, a 250 bp band amplified from RNA and a 450 bp band amplified from the DNA contaminating plasma RNA extract, appeared on the gel. All three samples yielded both 250 and 450 bp bands in the presence of RT (FIG. 1b, lanes 13-15), and a single 450 bp band was observed from a RNase treated DNA sample in the absence of RT (FIG. 1b, lane 1).

Fifteen patients were tested with carcinoma using three slight different experimental settings described above, and the data showed that 15 in 15 patients were clearly positive for plasma β-catenin.

Example 2

Plasma RNA was Present at High Rates in Patients with Adenomas, but not in Healthy Individuals Seventeen plasma samples were screened for β-catenin RNA from individuals with suspected adenomas. Of the 17 plasma samples from individuals with suspected adenomas screened for β-catenin RNA, 11 were plasma positive, indicated by the presence of a 250 bp RT-PCR product; 6 were found negative (FIG. 2a, lanes 1-11; FIG. 2b, lanes 1-6). RT-PCR assays were performed on the 6 negative samples using primers specific for β-actin sequences (Table 2, Primer #3). β-actin RNA was detected in all six plasma samples (FIG. 2c, lanes 1-6), indicating the six plasma RNA extracts were in amplifiable quality. Of the 6 patients with negative β-catenin signals (Table 1, Patients #10, 14, & 16), biopsy later confirmed that three were diagnosed with adenoma, two had granulation tissues, and the other had a dilated lymphatic space (Table 1, Patients #1-3). The percentage of detection among adenoma patients was 79% (11 of 14). Parallel RT-PCR analyses were performed on 10 healthy subjects. Nine of the ten healthy controls showed negative plasma β-catenin signals, but all showed positive β-actin RNA signals (FIG. 2d & FIG. 2e, lanes 1-10). Only 1 of them had a rather weak positive signal (FIG. 2d, lane 10).

In summary, the presence of β-catenin was examined in the blood plasma of 32 patients with confirmed carcinoma or adenoma using RT-PCR analysis. Results showed that 100% (15 of 15) of patients with carcinoma, 79% (11 of 14) of patients with adenoma and 10% (1 of 10) healthy volunteers carried β-catenin RNA in their circulating blood. It is worthy to mention that the apparently healthy subject with weak plasma β-catenin RNA had been suffered from long-standing colorectal discomfort, occasionally with fecal blood and diarrhea, although no abnormality or ulceration colitis was detected in an endoscopic examination. Three patients with suspected adenoma at admission were also tested for plasma β-catenin. All three patients who were later confirmed by biopsy to be free of adenoma were negative for plasma signal.

It has been shown that free DNA is present in the circulating blood of patients with disorders and cancers, and this DNA can be detected using PCR assay.

Furthermore, reports have showed that genetic alterations of specific gene sequences can be detected in the serum of cancer patients (Anker P 1997; Hibi K 1998; Kopreski M S 2001; Sozzi G 1999; von Knobloch R 2001). Aside from plasma DNA, sequence-specific RNAs have also been detected in cancerous, but not healthy, individuals using RT-PCR analysis (Kopreski M S 1999; Lo K W, 1999; Chen X Q 2000). Whether the PCR method for the detection of plasma and serum DNA or RNA can be implemented for cancer diagnosis and prognosis will mainly depend on how well the data can validate the status of the tumor or even the pre-cancerous lesions. For instance, carcinoembryonic antigen (CEA) is expressed widely in a variety of cancers and in some normal tissue including colonic tissues. Along with carbohy-drate antigen 19-9 (CA 19-9), these are the two most common tumor markers in the management of patients with CRC. In general, CEA marker yields positive detection rates ranging from 40 to 60% by conventional immunochemical assay for protein content. The use of RT-PCR for serum CEA RNA detection have improved the detection rate from 35% to around 70% (Guadagni, 2001), Another recent study has showed that tyrosine mRNA is present in the serum of 60% (4 of 6) patients with malignant melanoma, but not in any normal control serum (Kopreski, 1999). In our current study, the positive rate for CRC detection is 100% for patients with carcinoma and 79% for patients with adenoma. Thus, the plasma β-catenin RNA seems to be an effective serum marker for CRC detection.

At present, the only non-invasive method for CRC screening is fecal occult blood testing (FOBT). Several studies found that screening with FOBT in average and high-risk patients reduced the mortality rate by 16%. The limitation of the test, however, is the low predictive rate (less than 20%). The other method used for CRC screening, in particular for early detection of adenomas, is flexible sigmoidoscopy, which is claimed to have reduced the mortality rate by 70% in few of the case-control studies (for reviews, see Scotiniotis I, 1999). The test is sensitive and specific; however, it is invasive in nature. In this regard, the RT-PCR-based method for the detection of serum β-catenin may indeed provide an ideal tool for CRC screening of average and high-risk individuals. This method can be applied to monitoring post-operation and chemotherapy patients. Since β-catenin is also known to be involved in other types of cancer, our current invention for detection serum or plasma β-catenin can be extended for the detection, monitoring, screening of cancers with different tissue origins. This is the first time the presence of plasma β-catenin RNA has been reported and been suggested to have diagnostic value.

Example 3

Immunochemical Staining of Nuclear β-catenin Signals of the Adenoma and Carcinoma Tissues In more than 200 cases examined, 92% of adenomas and 100% of carcinomas, but none of the normal tissues showed elevated nuclear β-catenin. To determine the nuclear β-catenin signals of the adenomas and carcinomas obtained from patients derived from Examples 1 & 2, paraffin-embedded tissue blocks of adenoma and carcinoma of 32 patients were sectioned and examined for nuclear β-catenin. The immunohistochemical staining was scored based on both the intensity and the percentage positive cells. Table 2 showed that nuclear translocation of β-catenin was observed in all tissue specimens.

Example 4

Quantification of Blood β-Catenin RNA in Healthy Individuals and Patients with Adenoma or Carcinoma Using Real Time RT-PCR Technology The quantitative difference in plasma β-catenin signal between adenoma and carcinoma patients was investigated using real-time reverse transcriptase-PCR (RT-PCR). The results showed that the average copy number of β-catenin mRNA was 30 fold higher in adenoma (n=12; 3 negative; 8 positive: mean, $1.1 \times 10^3$; ranging from $0.69 \times 10^3$ to $1.80 \times 10^3$) and 598 fold higher in carcinoma (n=18; mean, $2.2 \times 10^4$ ranging from $0.67 \times 10^4$ to $4.4 \times 10^4$) patients than the normal individuals ((n=14; mean, 36 ranging from 0 to 169). The copy number of β-catenin mRNA in carcinoma patients was 19 fold higher than in adenoma patients. These quantification analysis provide a clear evidence that the plasma β-catenin mRNA are present differentially and can be used as a diagnostic tool to differentiate healthy subject, adenoma and carcinoma patients.

Example 5

Detection of β-catenin DNA in the serum of patients with colorectal adenoma and carcinoma PCR analysis was first performed with serum DNA samples extracted from colorectal carcinoma patients. The results showed that a 359 bp band was observed in all 15 serum DNA samples. Ten patients were tested with confirmed adenoma ranging from mild to severe dysplasia. A positive band was detected in 9 of 10 patients. The detection rate was 90%. The only negative case was amplifiable as it yielded positive 156 bp band after amplification with RET specific primers PCR amplification of β-catenin was also performed on 10 healthy volunteer controls. None of the serum samples showed positive signals for β-catenin, while positive signals were clearly detected using RET specific primers. In addition, a known positive carcinoma serum sample was carried out in parallel and showed typical 359 bp band on the agarose gel (data not shown). These results demonstrate the ability of β-catenin to accurately detect colorectal carcinoma and adenoma.

The data showed, for the first time, that serum β-catenin DNA is detectable in all patients with colorectal carcinoma and in 9 out of 10 patients with colorectal adenoma, while all 10 healthy individuals were free of serum β-catenin DNA. This result suggests that the presence of β-catenin DNA in the blood is significantly correlated with the existence of cancer at both preneoplastic and malignant stages, which may also suggest that the circulating β-catenin originated from the adenoma or carcinoma tissue of the patients. The ten adenoma patients, the individual (Patient #9, Table 4) negative in serum β-catenin had the smallest adenoma in this example (3.5 mm in diameter, 48 $mm^3$)). Patient with the next smallest size of adenoma (63 $mm^3$) showed PCR amplifiable β-catenin DNA in the blood, suggesting that the sensitivity of the current method would allow us to detect premalignant adenomotous polyps at least as small as 63 $mm^3$. Quantification of the copy number of β-catenin DNA in the samples using real-time PCR analysis is suggested. The findings indicate that measuring the levels of β-catenin DNA in the blood provides a highly sensitive but noninvasive method for early detection of colorectal cancer. This method may be extended to cancers of different tissue origins.

Referring now to the drawings, FIG. 1 collectively shows detection of β-catenin RNA from plasma of colorectal carcinoma patients using RT-PCR. More specifically, FIG. 1a shows RT-PCR amplification of β-catenin using β-catenin exon primers. Lanes 1-4, RT-PCR reactions of blood RNA samples isolated from two carcinoma patients in the presence (Lane 1 & 3) and absence (Lane 2 & 4) of RT enzyme; Lane 5, mRNA extracted from carcinoma specimen expressing β-catenin as a positive control; Lane 6, a buffer control. M: RNA markers. FIG. 1b shows RT-PCR amplification of β-catenin using β-catenin intron-spanning primers. Lanes 1-10, DNAase-treated plasma RNAs isolated forum ten carcinoma patients; Lane 11 genomic DNA as a positive control for PCR reaction; Lane 12, a buffer control. Lanes 13-17, Samples derived from Lanes 8-12 respectively without prior DNAase treatment. FIG. 1c shows Lane 1-3, β-catenin RNA (250 bp) isolated from three patients by RT-PCR with intron-spanning primers without DNAase treatment; lane 4, positive DNA control; lane 5, negative buffer control. M: DNA markers.

FIG. 2 shows detection of blood β-catenin (FIG. 2a & FIG. 2b) & β-actin (FIG. 2c) RNA from patients suspicious for colorectal adenoma (FIG. 2a-2c) using RT-PCR. A. Lanes 1-17, plasma RNAs isolated from 17 patients; Lane 18, positive DNA control; Lane 19, negative control. Detection of blood β-catenin (FIG. 2d) & β-actin (FIG. 2e) RNA from plasma of ten healthy objects (Lanes 1-10). Lane 11, positive DNA control, Lane 12, negative buffer control.

FIG. 3 shows detection of serum β-catenin DNA from patients with adenomas or carcinomas and normal controls. FIG. 3a, FIG. 3b and FIG. 3c show PCR analyses with β-catenin specific primers were performed with serum samples isolated from patients with colorectal carcinoma: FIG. 3a, lanes 1-15; with colorectal adenoma: FIG. 3b, lanes 1-10; from healthy individuals: FIG. 3c, lanes 1-10. FIG. 3d: PCR reactions with RET specific primers were performed with serum samples with negative β-catenin signal. Lanes 1-10, same healthy individual serum samples shown in FIG. 3c; FIG. 3d, lane 13: the same serum sample shown in Panel FIG. 3b, lane 8. Positive control genomic DNA isolated from carcinoma tumor: FIG. 3a, lane 16; FIG. 3b, lane 11; FIG. 3c, lane 11; FIG. 3d, lane 11. Negative cell free control: FIG. 3a, lane 17; FIG. 3b, lane 12; FIG. 3c, lane 12; FIG. 3d, lane 12. M: Hae III λ DNA marker.

Techniques Applied

Blood Samples and RNA Extraction

A 6-ml blood sample was collected from each patient by transcutaneous needle into 8-ml Vacutaniners containing EDTA lithium heparin. Blood samples were centrifuged at 4800 rpm for 8 min. Plasma was aliquoted into polypropylene tubes and stored at −80° C. for later RNA extraction. RNA was extracted from plasma sample using TRIZOL Kit (Life Technologies, USA), then purified with RNeasy column (Qiagen, Germany) according to the manufacturer's manuals. In brief, 2 ml of each plasma sample was mixed with 1.6 ml TRIZOL and 0.4 ml chloroform, centrifuged at 12,000 rpm for 15 min at 4° C. The aqueous phase was collected for RNA extraction using the RNeasy column. The isolated RNA was dissolved in 15 µl of DEPC-treated water. The RNA samples were farther treated with PCR grade of deoxyribonuclease I (DNase I)(Life Technologies). In the reaction, 1 µl each of 10×DNase I reaction buffer and DNase I were added into the 15 µl of RNA sample and incubated at room temperature for 15 min followed by inactivation of DNase I by the addition of 1 µl of 15 mM EDTA and heated at 65° C. for 5 min, then chilled in ice before RT-PCR reaction.

Primers and RT-PCR Reactions of Blood RNA Samples

The detection of plasma β-catenin was performed using RT-PCR assay with a set of primers including intron sequence spanning between exon 3 and 4 of β-catenin gene (Table 1). For comparison, a separate set of primers sequences within exon 3 of the β-catenin gene was also incorporated in some PCR reactions. The reverse transcription reaction was performed according to the manufacturer's guides (Qiagen, Germany). PCR was carried out using reagents supplied in a GeneAmp DNA Amplification Kit using AmpliTaq Gold as the polymerase (Perkin-Elmer Corp., Foster City, Calif.). The parameters used in PCR were 40 cycles with initial denaturation at 95° C. for 10 min, followed by 94° C. for 1 min 15 s, 59° C. (β-catenin) for 1 min 30 s, 72° C. for 1 min 30 s, with a final extension step of 72° C. for 10 min. PCR products were analyzed by 1.5% agarose gel electrophoresis and ethidium bromide staining. A negative (water) control was included in each RT-PCR assay. All samples with negative results were subjected to RT-PCR assay for β-actin RNA using intron-spanning primers (Table 3) as a control for the amplifiability of plasma-extracted RNA.

DNA Extraction

Blood sera were removed from the supernatants of clotted blood samples and were centrifuged at 4800 rpm for 8 minutes, followed by gently aliquoting of serum into polypropylene tubes and storage at −20° C. for later DNA extraction. DNA was isolated from 200 µl serum using QIAamp DNA Mini Kit (Qiagen, Hilden Germany) according to the manufacturer's protocol. The DNA samples, were eluted with 50 µl of ddH20.

Primers and PCR Reactions of Blood DNA Samples

The detection of β-catenin was performed using PCR assay with set of primers franking the $2^{nd}$ and the $3^{rd}$ introns of β-catenin gene (Table 3). The PCR was carried out using reagents supplied in a GeneAmp DNA Amplification Kit using AmpliTaq Gold as the polymerase (Perkin-Elmer Corp., Foster City, Calif.). The parameters used in PCR were 40 cycles with initial denaturation at 95° C. for 10 min, followed by 94° C. for 1 min and 15 s, 57° C. (β-catenin) and 69° C. (RET) for 1 min 30 s, 72° C. for 1 min 30 s, with a final extension step of 72° C. for 10 min. PCR products were analyzed by 1.5% agarose gel electrophoresis and ethidium bromide staining. PCR products were confirmed by direct DNA sequencing. A negative (water) control was included in each PCR assay. All samples with negative results were subjected to PCR assay for RET gene as a control for the amplifiable quality of the serum DNA samples. The RET gene sequence which encodes receptor tyrosine kinase, is normally present in circulating blood of healthy individuals (Matisa-Guiu 1998).

Immunohistochemical Staining and Evaluation

Monoclonal antibody to β-catenin (C19220) was purchased from Transduction Laboratories (U.S.A.). The antibody was produced against the C-terminal of a mouse catenin protein (a.a. 571-581), and is reactive to β-catenin of human, rat and mouse species. Tissue sections with 4 µm thickness were placed on silane-coated (Sigma Chemicals, St. Louis, Mo.) glass slides, air dried overnight and rehydrated with xylene and graded alcohol. Antigen retrieval and immunochemical staining was performed in the Ventana-ES automated immunostainer (Ventana, Tucson, Ariz.) as described. The sections were counterstained with Harris haematoxylin and mounted with permount after dehydration in graded alcohol. The negative control was done by replacing β-catenin antibody with TBS. Positive signals were evaluated in 4 fields under a light microscope at 10×40 magnification, without knowledge of the clinical outcome. The results were evaluated by two independent observe manually and the data were expressed as IHC score obtained by multiplying "percentage of positive cells" by "staining intensity" according to Remmele and Schicketanz with slight modification (Remmele & Schicketanz, 1993; Wong et al., 2001). In this study, the IHC scores were presented as follows: "−"=no expression, 1+=weak expression, 2+=moderate expression 3+=strong expression and 4+=very strong expression.

Quantitative Analysis of Plasma β-catenin RNA by Real-Time RT-PCR

Copy numbers of plasma β-catenin RNA were measured by real-time RT-PCR, using the TaqMan detection system (Heid et al., 1996). The amount of fluorescent product at any given cycle within the exponential phase of PCR is proportional to the initial number of template copies. The reactions were recorded and analyzed using an ABI Prism 7700 sequence detector equipped with a 96-well thermal cycler (Perkin-Elmer Applied Biosystems, UK). Briefly, RNA samples (50-100 ng) were incubated with 0.01 units of uracil N-glycosylase (2 min at 50° C.) and reverse-transcribed in a 25-μl oligo(dT)-primed reaction at 60° C. for 30 min. The cDNA templates were then subjected to a 5-min initial denaturation at 92° C. prior to 40 cycles of PCR (92° C. for 20 s and 62° C. for 1 min, per cycle) in the presence of forward and reverse primers, then labeled with the fluorescent quenching group 6-carboxyfluorescein at the 5' end and the fluorescent quencher molecule at the 3' end.

TABLE 1

Sequence of primers used in the PCR reactions.

| Primer | Nucleotide sequence (5' to 3') | Design | product size |
|---|---|---|---|
| 1 | sense: ATTTGATGGAGTTGGACATGG (SEQ ID NO: 4) antisense: AGCTACTTGTTCTTGAGTGAA (SEQ ID NO: 5) | Within exon 3 of β-Catenin gene | 224 bp |
| 2 | sense: TGATTTGATGGAGTTGGACAT (SEQ ID NO: 6) antisense: CATTGCATACTGTCCATCAAT (SEQ ID NO: 7) | Intron-spanning between exon 3 & 4 of β-Catenin gene | DNA: 450 bp cDNA: 250 bp |
| 3 | sense: AAATCGTGCGTGACATTAAGG (SEQ ID NO: 8) antisense: ATGATGGAGTTGAAGGTAGTT (SEQ ID NO: 9) | Intron-spanning between exon 4 & 5 of β-actin gene | DNA: 324 bp cDNA: 230 bp |

TABLE 2

Correlation of plasma β-catenin RNA in colorectal adenoma and carcinoma patients with nuclear β-catenin expression (IHC scores) in their respective lesions.

| Patients | Sex | Age | Diagnosis | Duke's stage | Size of lesion | Plasma β-catenin | IHC of β-catenin |
|---|---|---|---|---|---|---|---|
| 1 | F | 65 | granulation tissue | N.A. | N.A. | − | − |
| 2 | F | 68 | granulation tissue | N.A. | N.A. | − | − |
| 3 | F | 59 | dilated lymphatic space | N.A. | N.A. | − | − |
| 4 | F | 68 | adenoma, moderate dys | N.A. | N.A. | + | + |
| 5 | F | 75 | adenoma, mild dys | N.A. | N.A. | + | ++ |
| 6 | M | 82 | adenoma, mild dys | N.A. | N.A. | + | + |
| 7 | F | 61 | adenoma, moderate dys | N.A. | 5 mm | + | + |
| 8 | M | 68 | adenoma, moderate dys | N.A. | 4 mm | + | + |
| 9 | F | 77 | adenoma, moderate dys | N.A. | N.A. | + | ++ |
| 10 | M | 72 | adenoma, moderate dys | N.A. | 10 mm | − | ++ |
| 11 | M | 51 | adenoma, mild dys | N.A. | N.A. | + | + |
| 12 | F | 81 | adenoma, moderate dys | N.A. | N.A. | + | + |
| 13 | M | 67 | adenoma, moderate dys | N.A. | 72 mm$^3$ | + | ++ |
| 14 | M | 75 | adenoma, moderate dys | N.A. | 672 mm$^3$ | − | ++ |
| 15 | M | 70 | adenoma, mild dys | N.A. | N.A. | + | + |
| 16 | M | 78 | adenoma, severe dys | N.A. | 1500 mm$^3$ | − | +++ |
| 17 | F | 73 | adenoma, severe dys | N.A. | 1200 mm$^3$ | + | +++ |
| 18 | M | 59 | adenocarcinorna | B | 91 cm$^3$ | + | + |
| 19 | F | 56 | adenocarcinoma | C | 90 cm$^3$ | + | + |
| 20 | F | 67 | adenocarcinoma | C | 108 cm$^3$ | + | + |
| 21 | F | 75 | adenocarcinoma | C | 100 cm$^3$ | + | ++++ |
| 22 | F | 92 | adenocarcinoma | N.A. | N.A. | + | ++++ |
| 23 | F | 79 | adenocarcinoma | N.A. | N.A. | + | ++ |
| 24 | F | 76 | adenocarcinoma | B | 88 cm$^3$ | + | ++ |
| 25 | M | 82 | adenocarcinoma | D | 115 cm$^3$ | + | + |
| 26 | F | 77 | adenocarcinoia | B | 346 cm$^3$ | + | + |
| 27 | F | 73 | adenocarcinoma | A | 21 cm$^3$ | + | ++++ |
| 28 | F | 82 | adenocarcinoma | N.D. | N.D. | + | ++++ |
| 29 | F | 80 | adenocarcinoma | B | 130 cm$^3$ | + | ++ |
| 30 | M | 77 | adenocarcinoma | B | 155 cm$^3$ | + | +++ |
| 31 | M | 62 | adenocarcinoma | B | 167 cm$^3$ | + | ++ |
| 32 | F | 85 | adenocarcinoma | B | 143 cm$^3$ | + | +++ | dys: dysplasia;
N.A.: not applied;
N.D.: not determined.

TABLE 3

Primers used in the PCR reactions.

| Primer | Nucleotide sequence (5' to 3') | Design | Product size |
|---|---|---|---|
| 1 | sense: TCAATGGGTCATATCACAGAT (SEQ ID NO: 10) CTGCATTCTGACTTTCAGTAA (SEQ ID NO: 11) | In intron 2 and 3 of β- | 359 bp |
| 2 | sense: CCTCTGCGGTGCCAAGCCTC (SEQ ID NO: 12) antisense: TGTGGGCAAACTTGTGGTAGCA (SEQ ID NO: 13) | Within exon 11 of RET gene | 156 bp |

TABLE 4

Patients record

| Patient | Sex | Age | Diagnosis | Duke's stage | Size of lesion |
|---|---|---|---|---|---|
| 1 | M | 23 | adenoma, severe dys | N.A. | 75 mm$^3$ |
| 2 | F | 48 | adenoma, moderate dys | N.A. | N.A. |
| 3 | M | 67 | adenoma, moderate dys | N.A. | 168 mm$^3$ |
| 4 | M | 67 | adenoma, severe dys | N.A. | 80 mm$^3$ |
| 5 | M | 76 | adenoma, severe dys | N.A. | 63 mm$^3$ |
| 6 | F | 62 | adenoma, mild dys | N.A. | N.A. |
| 7 | M | 85 | adenoma, severe dys | N.A. | 153 mm$^3$ |
| 8 | F | 81 | adenoma, moderate dys | N.A. | 96 mm$^3$ |
| 9 | F | 58 | adenoma, moderate dys | N.A. | 48 mm$^3$ |
| 10 | F | 68 | adenoma, moderate dys | N.A. | 528 mm$^3$ |
| 11 | M | 62 | adenocarcinoma | B | 182 cm$^3$ |
| 12 | M | 67 | adenocarcinoma | B | 72 cm$^3$ |
| 13 | M | 83 | adenocarcinoma | B | 43 cm$^3$ |
| 14 | M | 45 | adenocarcinoma | C | 67 cm$^3$ |
| 15 | M | 52 | adenocarcinoma | C | 41 cm$^3$ |
| 16 | F | 71 | adenocarcinoma | C | 64 cm$^3$ |
| 17 | M | 80 | adenocarcinoma | C | 47 cm$^3$ |
| 18 | M | 61 | adenocarcinoma | N.D. | N.A. |
| 19 | F | 70 | adenocarcinoma | A | 13 cm$^3$ |
| 20 | M | 69 | adenocarcinoma | B | 120 cm$^3$ |
| 21 | M | 61 | adenocarcinoma | C | 384 cm$^3$ |
| 22 | F | 72 | adenocarcinoma | A | 9 cm$^3$ |
| 23 | M | 76 | adenocarcinoma | N.D. | N.A. |
| 24 | M | 76 | adenocarcinoma | C | 88 cm$^3$ |
| 25 | M | 70 | adenocarcinoma | B | 23 cm$^3$ | dys: dysplasia;
N.A.: not applied;
N.D.: not determined

While various embodiments are disclosed herein, it should be understood that they have been presented by way of example only, and not limitation. Thus, the breadth and scope of the invention(s) should not be limited by any of the above-described exemplary embodiments, but should be defined only in accordance with the following claims and their equivalents. Moreover, the above advantages and features are affected in described embodiments, but shall not limit the application of the claims to processes and structures accomplishing any or all of the above advantages. Furthermore, teachings from the following references are incorporated herein by reference for all purposes:

Anker, P., Lefort, F., Vasioukhin, V., Lyautey, I., Lederrey, C., Chen, X. Q., Stroun, M., Mulcahy, H. E. and Farthing, M. J. K-ras mutations are found in DNA extracted from the plasma of patients with colorectal cancer. Gastroenterology 112:1114-1120, 1997.

Chen, X. Q., Bonnefoi, H., Pelte, M-F., Lyautey, J., Lederrey, C., Movarekhi, S., Schaeffer, P., Mulcahy, H. E., Meyer, P., Stroun, M. and Anker, P. Telomerase RNA as a detection marker in the serum of breast cancer patients. Clinical Cancer Research 6: 3823-3826, 2000.

Hibi, K., Robinson, C. R., Booker, S., Wu, L., Hamilton, S. R., Sidransky, D. and Jen, J. Molecular detection of genetic alterations in the serum of colorectal cancer patients. 58:1405-1407, 1998.

Kopreski, M. S., Benko, F. A., Kwak, L. W. and Gocke, C. D. Detection of tumor suppressor messenger RNA in the serum of patients with malignant melanoma. Clinical Cancer Research 5: 1961-1965, 1999.

Kopreski, M. S., Benko, F. A and Gocke, C. D. Circulating RNA as a tumor marker: detection of 5T4 mRNA in breast and lung cancer patient serum Ann. N.Y. Acad. Sci. 945: 172-178, 2001.

Lo, K. W., Lo, Y. M. D., Leung, S. F., Tsang, Y. S., Chan, L. Y. S., Johnson, P. J., Hjelm, N. M., Lee, J. C. K. and Huang, D. P. Analysis of cell-free Epstein-Barr virus-associated RNA in the plasma of patients with nasopharyngeal carcinoma. Clinical Chemistry 45: 1292-1294, 1999.

Matias-Guiu, X. RET protooncogene analysis in the diagnosis of medullary thyroid carcinoma and multiple endocrine neoplasia type II. Advances in Anatomic Pathology 5: 196-201, 1998.

Morin, P. J. β-catenin signaling and cancer. Bioessays, 21: 1021-1030, 1999. Remmele, W., Schicketanz, K. H. Immunohistochemical determination of estrogen and progesterone receptor content in human breast cancer. Computer-assisted image analysis (QIC score) vs subjective grading IRS. Pathol Res Pract 189: 862-866, 1993.

Sozzi, G., Musso, K., Ratcliffe, C., Goldstraw, P., Pierotti, M. A. and Pastorino, U. Detection of microsatellite alterations ill plasma DNA of non-small cell lung cancer patients: a prospect for early diagnosis. Clin. Cancer Res. 5: 2689-2692, 1999.

von Knobloch, R., Hegele, A., Brandt, H., Olbert, P., Heidenreich, A. and Hofman, R. Serum DNA and urine DNA alterations of urinary transitional cell bladder carcinoma detected by fluorescent microsatellite analysis. Int. J. Cancer 94: 67-72, 2001.

Willert, K. and Nusse, R. β-catenin: a key mediator of Wnt signaling. Curr. Opin, Genet. Dev. 8: 95-102, 1998.

Wong, S. C., Chan, K. C., Lee, K. C., Hsiao, W. L. Differential expressions of p16/p21/p27 and cyclin D1/D3, and their relationships to cell proliferation, apoptosis and tumor progression in invasive breast ductal carcinoma. J Pathol 194: 35-42, 2001.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field of the Invention," the claims should not be limited by the language chosen under this heading to describe the so-called field of the invention. Further, a description of a technology in the "Background of the Invention" is not to be construed as an admission that technology is prior art to any invention(s) in this disclosure. Neither is the "Brief Summary of the Invention" to be considered as a characterization of the invention(s) set forth in the claims set forth herein. Furthermore, the reference in these headings, or elsewhere in this disclosure, to "invention" in the singular should not be used to argue that there is only a single point of novelty claimed in this disclosure. Multiple inventions may be set forth according to the limitations of the multiple claims associated with this disclosure, and the claims, and their equivalents, accordingly define the invention(s) that are protected thereby. In all instances, the scope of the claims shall be considered on their own merits in light of the specification, but should not be constrained by the headings set forth herein.

What is claimed is:

1. A method for detecting colorectal carcinoma in a human patient, comprising:
   a) extracting blood serum or plasma from the patient;
   b) measuring an amount of beta-catenin nucleic acid in the blood serum or plasma; and
   c) determining a possibility of the presence of colorectal cancer in the patient based on the amount of the nucleic acid measured in the blood serum or plasma.

2. The method according to claim 1, wherein the nucleic acid is beta-catenin RNA.

3. The method according to claim 1, wherein the nucleic acid is beta catenin DNA.

4. The method according to claim 2, wherein measuring the amount of beta-catenin RNA is carried out with a RT-PCR method which amplifies a nucleic acid fragment corresponding to a portion of beta-catenin gene.

5. The method according to claim 4, wherein the RT-PCR method uses a pair of primers identified as SEQ ID NO: 4 and SEQ ID NO: 5.

6. The method according to claim 4, wherein the RT-PCR method uses a pair of primers identified as SEQ ID NO:6 and SEQ ID NO:7.

7. The method according to claim 4, wherein the RT-PCR method uses a pair of primers identified as SEQ ID NO:8 and SEQ ID NO:9.

8. The method according to claim 3, wherein measuring the amount of beta-catenin DNA is carried out with a PCR method which amplifies a nucleic acid fragment corresponding to a portion of beta-catenin gene.

9. The method according to claim 8, wherein the PCR method using a pair of primers flanking the $2^{nd}$ and $3^{rd}$ introns of beta-catenin gene.

10. The method according to claim 9, wherein the pair of primers is identified as SEQ ID NO:10 and SEQ ID NO:11.

11. The method according to claim 1, wherein a volume of the blood serum or plasma used is from 2 ml to 5 ml.

* * * * *

UNITED STATES PATENT AND TRADEMARK OFFICE
CERTIFICATE OF CORRECTION

PATENT NO.       : 7,811,752 B2                                             Page 1 of 1
APPLICATION NO.  : 10/516864
DATED            : October 12, 2010
INVENTOR(S)      : Wen-Luan Wendy Hsiao and Sze-Chuen Cesar Wong It is certified that error appears in the above-identified patent and that said Letters Patent is hereby corrected as shown below:

In column 11, Table 3, under "(SEQ ID NO: 10)", insert -- antisense: --; and

In column 11, Table 3, after "In intron 2 and 3 of β-", insert -- Catenin gene --.

Signed and Sealed this
Fourth Day of January, 2011

David J. Kappos
*Director of the United States Patent and Trademark Office*